United States Patent [19]
Legzdins et al.

[11] Patent Number: 5,811,463
[45] Date of Patent: Sep. 22, 1998

[54] COMPOSITIONS AND METHOD FOR RELAXING SMOOTH MUSCLES

[75] Inventors: Peter Legzdins, West Vancouver; Catherine C. Y. Pang, Vancouver; Michael J. Shaw, Cowansville, all of Canada

[73] Assignee: University of British Columbia, Vancouver, Canada

[21] Appl. No.: 770,559

[22] Filed: Dec. 20, 1996

Related U.S. Application Data

[63] Continuation of Ser. No. 132,632, Oct. 6, 1993, Pat. No. 5,631,284.

[51] Int. Cl.$^6$ .......................... A61K 31/13; A61K 31/04; A61K 31/28
[52] U.S. Cl. .......................... 514/645; 514/740; 514/505; 514/492
[58] Field of Search ...................................... 514/505, 492, 514/645, 740; 564/300, 301; 424/646, 649, 655

[56] References Cited

U.S. PATENT DOCUMENTS

| | | | |
|---|---|---|---|
| 3,422,144 | 1/1969 | Hoffman et al. | 564/300 |
| 3,480,653 | 11/1969 | Pande et al. | 564/301 |
| 4,571,391 | 2/1986 | Riley et al. | 514/4 |
| 4,748,160 | 5/1988 | Bennion et al. | 514/82 |
| 5,366,997 | 11/1994 | Keefer et al. | 514/611 |

OTHER PUBLICATIONS

Butler, Anthony R. and Williams, D. Lyn H., "The Physiological Role of Nitric Oxide," *Chem. Soc. Rev.* 22(4):233–241, 1993.

Clarke, M. J. and Gaul, J. B., "Chemistry Relevant to the Biological Effects of Nitric Oxide and Metallonitrosyls," *Struct. Bonding (Berlin)* 81:147–181, 1993.

*Primary Examiner*—Deborah Lambkin
*Attorney, Agent, or Firm*—Seed and Berry LLP

[57] ABSTRACT

Compositions and methods for relaxing smooth muscle in a warm-blooded animal are provided, comprising the step of administering to the animal a transition-metal nitrosyl complex. In one aspect, the transition-metal nitrosyl complex is represented by the formula $L_3M(NO)_yX_{3-y}$ where L is a two-electron Lewis base or $L_3$ is a six-electron Lewis base, M is a Group 6 or 8 transition-metal, and when y is 1, X is carbon monoxide, and when y is 2, X is a halide or pseudohalide. In another aspect, the transition-metal nitrosyl complex is represented by the formula $[M(NO)_2X_y]_2$ where X is a halide or pseudohalide, and when M is a Group 6 transition-metal, y is 2, and when M is a Group 8 transition-metal, y is 1. Methods are also described for treating hypertension, angina pectoris, congestive heart disease, and impotence utilizing pharmaceutical compositions comprising the above-described transition-metal nitrosyl complexes.

14 Claims, 2 Drawing Sheets

COMPOSITIONS AND METHOD FOR RELAXING SMOOTH MUSCLES

CROSS-REFERENCE TO RELATED APPLICATION

This application is a continuation of U.S. patent application Ser. No. 08/132,632, filed Oct. 6, 1993, U.S. Pat. No. 5,631,284.

TECHNICAL FIELD

The present invention relates generally to compositions and methods of relaxing smooth muscles and, more specifically, to compositions and methods which utilize transition-metal nitrosyl compounds as smooth muscle relaxants.

BACKGROUND OF THE INVENTION

Muscle is divided into three types: skeletal, cardiac, and smooth. Briefly, smooth muscle is found in all muscles where contraction is involuntary, except for heart muscle. Generally, smooth muscle is composed of elongated, spindle-shaped, nucleated cells arranged parallel to one another and to the long axis of the muscle.

Smooth muscle is classified both functionally, and anatomically. When classified functionally, it is broken into two groups: multi-unit, and single-unit smooth muscle. Briefly, multi-unit smooth muscle is activated by nerves which cause contraction of independent muscle units, and thus is not spontaneously active. Examples of multi-unit muscle may be found in large arteries and veins, the urinary bladder, and the iris and ciliary muscles of the eye. In contrast to multi-unit smooth muscle, single- unit smooth muscle is usually spontaneously active, and contains tight junctions which facilitate the contraction of the muscle as a single unit. Examples of single-unit smooth muscle may be found in the vasculature (small veins, small arteries, and arterioles), the bile duct, and the walls of the gastrointestinal and urinogenital systems (gut, ureter, and uterus).

When smooth muscle is anatomically classified, it is generally divided into two groups: vascular and non-vascular. Briefly, vascular smooth muscle consists only of blood vessels (arteries, arterioles, and veins), whereas non-vascular muscle includes all other types of smooth muscle (e.g., gastrointestinal (stomach, duodenum, ileum, jejunum, caecum, and colon), spleen, trachea/bronchus, seminal vesicle, ductus deferens, corpus cavernosum, biliary tract, ureter, and uterus).

Many diseases are characterized by the inability of smooth muscle to relax. For example, hypertension is a disease found in 15%–20% of all adults in the United States. This condition is characterized by persistently high arterial blood pressure which, if left untreated, may lead to other serious cardiovascular diseases such as heart failure, ischemia, renal failure, and stroke. Hypertension is one of the most important public health problems facing developed countries.

Because of the health risk associated with untreated hypertension, the importance of treating those who suffer from elevated blood pressure has been recognized. Clinical trials have shown that appropriate pharmacological treatment of patients with moderate or severe hypertension reduces the risk of stroke, renal failure, and congestive heart failure. Based upon these studies, patients are now commonly treated with antihypertensive drugs in order to lower diastolic blood pressure ("DBP") to levels below 90 mmHg. Common drugs which are used for this purpose include diuretics (hydrochlorothiazide, chlorthalidone), sympatholytics (clonidine, atenolol, prazosin), vasodilators (minoxidil, sodium nitroprusside), angiotensin converting enzyme inhibitors (captopril, enalapril), and calcium entry blockers (nifedipine, nitrendipine). The selection of a specific drug depends upon the severity of the disease, the patient's age and lifestyle, side effects, cost, and concomitant diseases and therapies.

One approach to the treatment of hypertension is to effect the reduction of elevated blood pressure through blood vessel dilation, which results in an increase of blood vessel diameter and concomitant blood pressure reduction. One class of compounds which are commonly utilized to dilate blood vessels are nitrovasodilators, which have been utilized for the relief of anginal attacks and the treatment of hypertension. Clinically useful nitrovasodilators include organic nitrites and nitrates such as amyl nitrite, glyceryl trinitrate (nitroglycerin), isosorbide dinitrate, erythrityl tetranitrate, and pentaerythritol as well as an inorganic nitric oxide donor, sodium nitroprusside.

Nitroglycerin and sodium nitroprusside are the most commonly used nitrovasodilators. Nitroglycerin is therapeutically useful for the treatment of angina pectoris and gastrointestinal spasm, while sodium nitroprusside is primarily utilized for the treatment of hypertensive emergencies. Nitroglycerin may either be administered at the time of anginal attack or prophylactically in anticipation of exercise or stress. Although nitroglycerin is effective in relief of acute attack, continual exposure to nitroglycerin and other organic nitrates results in a reduction in the ability of these compounds to vasodilate blood vessels. Because of the tolerance that develops from their chronic use, these nitrovasodilators have limited applicability.

Sodium nitroprusside is likewise effective in lowering blood pressure, although its use is primarily limited to hypertensive emergencies due to its efficacy and toxicity. In particular, the infusion of sodium nitroprusside at high doses or for long periods of time (over 24 hours) is associated with the toxicities resulting from the accumulation of cyanide and or thiocyanate.

Accordingly, there is a need in the art for physiologically acceptable smooth muscle relaxants which do not result in the development of tolerance and do not have toxic side effects. The present invention fulfills these needs, and further, provides other, related advantages.

SUMMARY OF THE INVENTION

Briefly stated, the present invention provides methods for relaxing smooth muscle in a warm-blooded animal, comprising the step of administering to the animal a therapeutically effective amount of a transition-metal nitrosyl complex. Within one aspect of the invention, the transition-metal nitrosyl complex is represented by the formula $L_3M(NO)_yX_{3-y}$ where L is a two-electron Lewis base or $L_3$ is a six-electron Lewis base, M is a Group 6 or 8 transition-metal, and when y is 2, X is either a halide or pseudohalide, and when y is 1, $X_2$ is either $L_2$ or XL.

Within another aspect of the invention, methods are provided for relaxing smooth muscle in a warm-blooded animal, comprising administering to the animal a transition-metal nitrosyl complex represented by the formula $[M(NO)_2X_y]_2$ where M is a Group 6 or 8 transition-metal, X is either a halide or pseudohalide, and when M is a Group 6 transition-metal, y is 2, and when M is a Group 8 transition-metal, y is 1.

A further aspect of the present invention provide methods for treating hypertension in a warm-blooded animal, comprising administering to the animal a therapeutically effective amount of a transition-metal nitrosyl complex represented by either the formula $L_3M(NO)_yX_{3-y}$ or $[M(NO)_2X_y]_2$ as described above.

Within another aspect of the present invention, methods for treating angina pectoris in a warm-blooded animal are provided, comprising administering to the animal a therapeutically effective amount of a transition-metal nitrosyl complex represented by either the formula $L_3M(NO)_yX_{3-y}$ or $[M(NO)_2X_y]_2$ as described above is disclosed.

A further aspect of the present invention provides methods for treating congestive heart failure in a warm-blooded animal, comprising administering to the animal a therapeutically effective amount of a transition-metal nitrosyl complex represented by either the formula $L_3M(NO)_yX_{3-y}$ or $[M(NO)_2X_y]_2$ as described above.

Within a further aspect of the present invention, methods for treating impotence in a warm-blooded animal are provided, comprising administering to the animal a therapeutically effective amount of a transition-metal nitrosyl complex represented by either the formula $L_3M(NO)_yX_{3-y}$ or $[M(NO)_2X_y]_2$ as described above is disclosed.

Another aspect of the present invention provides pharmaceutical compositions comprising a transition-metal nitrosyl complex and a pharmaceutically acceptable carrier or diluent. The transition-metal nitrosyl complex of the pharmaceutical composition may be represented by either the formula $L_3M(NO)_yX_{3-y}$ or $[M(NO)_2X_y]_2$ as described above. These pharmaceutical compositions may be utilized in the methods described above, as well as in a variety of in vitro and in vivo assays which are discussed in more detail below and in the Examples.

These and other aspects of the present invention will become evident upon reference to the following detailed description and attached drawings.

DETAILED DESCRIPTION OF THE INVENTION

Figure 1A:
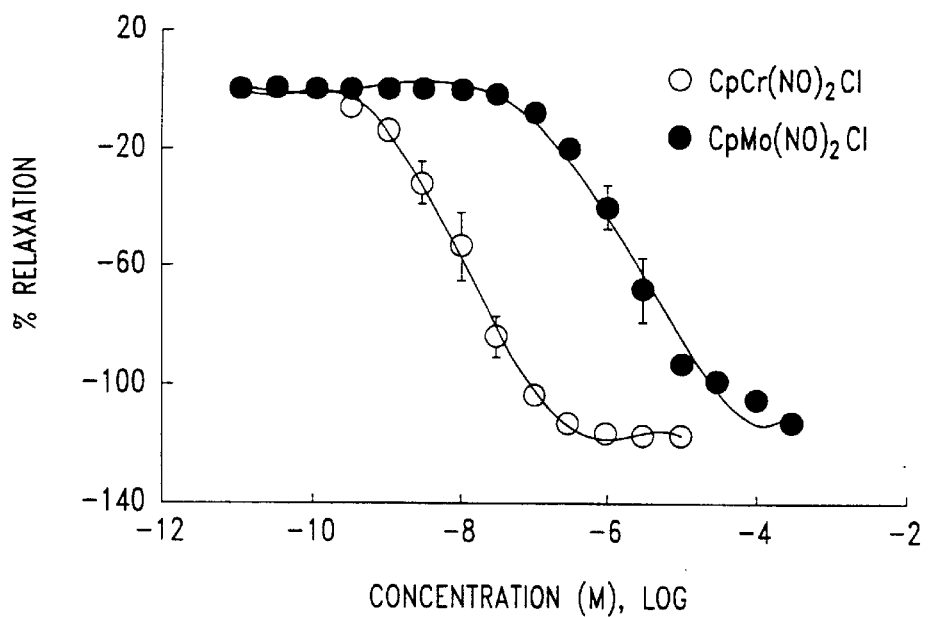
FIG. 1 is a graph which illustrates the effects of CpCr$(NO)_2$Cl and CpMo$(NO)_2$Cl on the relaxation of phenylephrine-preconstricted rat aortic rings (1A) and the change in mean arterial blood pressure in conscious rats (1B).

As noted above, the present invention is directed toward transition-metal nitrosyl complexes which are effective in relaxing smooth muscle in vivo, without the development of tolerance associated with organic nitrites and nitrates such as nitroglycerin, and without the toxic side effects of sodium nitroprusside. As smooth muscle relaxants, these transition-metal nitrosyl complexes are useful as pharmaceutical compositions for the treatment of a variety of conditions wherein it is desired to relax smooth muscles, including for example, hypertension, angina pectoris, congestive heart failure, and impotence, as well as a variety of in vitro and in vivo assays described below.

The transition-metal nitrosyl complexes of the present invention may be generally represented by the formula $L_3M(NO)_yX_{3-y}$ wherein L is a two-electron Lewis base or $L_3$ is a six-electron Lewis base, wherein M is a transition-metal, wherein X is a halide or a pseudohalide, and wherein if y is 1, X is carbon monoxide and if y is 2, X is a halide or pseudohalide. As used herein, the term "transition-metal nitrosyl complex" refers to a composition in which a transition-metal is coordinatively complexed with ligands wherein at least one ligand is nitric oxide. The term "nitrosyl" refers to the nitric oxide ligand. A transition-metal is defined as any metal that is a member of Periodic Groups 3–12. Preferred transition-metals include Groups 6 and 8 metals; chromium, molybdenum, tungsten, and iron, ruthenium, osmium, respectively. A more preferred embodiment of the present invention comprises transition-metals from Group 6. As represented by the formula $L_3M(NO)_yX_{3-y}$, the transition-metal ligands are L, NO (nitric oxide), and X wherein- L is a two-electron Lewis base or $L_3$ is a six-electron Lewis base and X is a halide or a pseudohalide, or alternatively, a two-electron Lewis base, L. As used herein, the term "Lewis base" refers to any chemical species which is an electron pair donor. Two-electron Lewis bases are those bases which may donated a single pair of electrons. Suitable two-electron Lewis bases include bases which bear atoms from Periodic Groups 15 and 16. Lewis bases from Group 15 contain nitrogen, phosphorous, arsenic, antimony or bismuth atoms as electron pair donors. Preferable Lewis base from Group 15 contain nitrogen, phosphorous, and antimony, and more preferably, nitrogen or phosphorous. Nitrogen containing Lewis bases include ammonia and its carbon substituted derivatives including primary, secondary, and tertiary amines and aromatic amines including pyridine and pyrrole as well as saturated analogs, piperidine and pyrrolidine. Other preferable nitrogen containing Lewis bases include amino acids and their derivatives. Phosphorous containing Lewis bases include phosphine and its carbon substituted derivatives including primary, secondary, and tertiary phosphines as well as alkoxy substituted derivatives including primary, secondary, and tertiary phosphites. Lewis bases from Group 16 contain oxygen, sulfur, or selenium atoms as electron pair donors. Preferable Lewis bases from Group 16 contain oxygen or sulfur. Oxygen containing Lewis bases include water and alcohols and sulfur containing bases include hydrogen sulfide and thiols. Carbon monoxide is also a two-electron Lewis base. The transition-metal nitrosyl complex may also have a six-electron Lewis base as ligand. As represented by $L_3M(NO)_yX_{3-y}$, $L_3$ may represent a six-electron Lewis base. Six-electron Lewis bases include bases such cyclopentadienyl anion and derivatives. In a preferred embodiment, the six-electron Lewis base is permethylcyclopentadienyl anion, and in a most preferred embodiment, the six-electron Lewis base is cyclopentadienyl anion. The transition-metal nitrosyl complex may also bear ligand X wherein X may be carbon monoxide where y is 1, and wherein X may be either a halide or pseudohalide where y is 2. Suitable halides include fluoride, chloride, bromide, and iodide. Preferred halides include chloride and iodide. Suitable pseudohalides include nitrite, nitrate, and cyanide anion.

In a preferred embodiment of the invention, the transition-metal nitrosyl complex may bear two nitrosyl ligands. In particular, the transition-metal nitrosyl complex represented by the general formula $L_3M(NO)_yX_{3-y}$ where y is 2 becomes $L_3M(NO)_2X$. In a most preferred embodiment, the six-electron Lewis base, $L_3$, is cyclopentadienyl anion; X may be selected from the group consisting of chlorides and nitro; and the transition-metal, M, may be selected from the group consisting of chromium, molybdenum, and tungsten.

In another preferred embodiment, the transition-metal may bear a single nitrosyl ligand. The transition-metal nitrosyl complex represented by the general formula $L_3M(NO)_yX_{3-y}$ where y is 1 becomes $L_3M(NO)X_2$. In a most preferred embodiment, the six-electron Lewis base, $L_3$, is cyclopentadienyl anion; X is carbon monoxide; and the transition-metal, M, may be selected from the group consisting of chromium, molybdenum, and tungsten.

In yet another embodiment, the transition-metal nitrosyl complex bears a single nitrosyl ligand and is represented by the formula $L_3M(NO)X_2$ where $X_2$ may be XL. Such a transition-metal nitrosyl complex is represented by the formula $L_3M(NO)XL$. In a most preferred embodiment the six-electron Lewis, base, $L_3$, is cyclopentadienyl anion; X is iodide; the two-electron Lewis base, L, may be selected from the group consisting of pyridine, piperidine, and trimethylphosphite; and the transition-metal, M, may be selected from the group consisting of chromium, molybdenum, and tungsten.

Within another aspect of the present invention, transition-metal nitrosyl complexes of the present invention may be represented by the formula $[M(NO)_2X_y]_2$ wherein M is a Group 6 or 8 transition metal, X is a halide or pseudohalide, and when M is a Group 6 transition-metal, y is 2, and when M is a Group 8 transition-metal, y is 1.

Some of the transition-metal nitrosyl complexes of the present invention are soluble in water and may be formulated as solutions in normal saline (0.9% sodium chloride). Water-insoluble complexes or complexes which have difficulty dissolving in water may be dissolved in 100% dimethylsulfoxide (DMSO), 60% DMSO in water, or 1:1 DMSO:Tween 80 followed by dilution with normal saline. Some complexes may require 10–20 minutes sonication to effect solution.

The transition-metal nitrosyl complexes of the present invention may be formulated as pharmaceutical compositions suitable for administration to a warm- blooded animal. Such formulations may contain an effective amount of the transition- metal nitrosyl complex as well as one or more pharmaceutically acceptable carriers and diluents. More specifically, the pharmaceutical compositions of the present invention may be administered as liquids, emulsions, or suspensions containing acceptable diluents such as alcohols and sterile water containing sugars, salts, preservatives, suspending agents, emulsifying agents, or administered as lotions, creams, or gels containing acceptable diluents, preservatives, or carriers to impart the desired texture, consistency, and viscosity. Such acceptable diluents and carriers are familiar to those skilled in the art, and include (but are not limited to) emulsifying agents such as non-ionic ethoxylated and non-ethoxylated surfactants, fatty alcohols, fatty acids, preserving agents, wax esters, triglyceride esters, steroid alcohols, phospholipids such as lecithin and cephalin, polyhydric alcohol esters, fatty acid esters, hydrophilic lanolin derivatives, hydrophobic beeswax derivatives, hydrocarbon oils (such as palm oil, coconut oil, and mineral oil), cocoa butter waxes, silicon oils, pH balancers, and cellulose derivatives. The present invention may be administered as tablets or capsules which may contain suitable diluents, or administered as inhalations, sprays or aerosols which may contain propellant, or aqueous or oily vehicles, or administered as suppositories which may contain cocoa butter, glycerinated gelatin or other suitable bases.

Preferably, pharmaceutical compositions of the present invention are formulated for the particular method of administration (e.g., intravenous, topical, pulmonary, rectal, sublingual, intramuscular, or oral), and in a manner which is in accordance with accepted practices, such as disclosed in *Remington's Pharmaceutical Sciences*, Gennaro, Ed., Mack Publishing Co., Easton, Pa. 1990 (which is incorporated herein by reference in its entirety). In addition, pharmaceutical compositions of the present invention may be placed within containers, along with packaging material which indicates that the pharmaceutical composition may be utilized to relax smooth muscles.

As noted above, the present invention also provides methods for relaxing smooth muscle in a warm-blooded animal (e.g., humans, chimps, cows, goats, pigs, dogs, cats, rats or mice) comprising the step of administering to the animal a therapeutically effective amount of a transition-metal nitrosyl complex as described above. Briefly, the efficacy (and therapeutically effective amount) of a particular transition-metal nitrosyl complex may be readily determined by both in vitro and in vivo techniques. See generally Blattner et al., *Experiments on Isolated Smooth Muscle Preparations*, Hugo Sachs Elektronik KG, 1980 (incorporated herein by reference in its entirety). For example, within one embodiment, a small animal such as a rat, rabbit, or guinea-pig is sacrificed and exsanguinated. The required tissue (e.g., artery, vein, stomach, ileum, jejunum, caecum, colon, uterus, spleen, trachea, seminal vesicle, ductus deferens, or corpus cavernosum) is removed and placed in an oxygenated physiological solution (e.g., Krebs or Tyrode solution). This tissue is then cut such that one end is attached to the bottom of a muscle bath, and the other end to a force-displacement transducer (for example, Grass FT-03-C, Quincy, Mass.) for isometric recording with a physiological recorder (Grass, Model 79G). An appropriate pre-load (0.5 to 10 grams, depending on the tissue) is then applied, and the tissue equilibrated in the bath for one hour prior to the start of the study.

The measurement of smooth muscle contractile response may then be performed essentially as described by Pang and Sutter in Blood Vessels 17:293–301, 1980 (incorporated herein by reference in its entirety). Briefly, a dose-response curve of an agonist (e.g., phenylephrine, norepinephrine) is first obtained by measuring contractile response of the muscle as a function of agonist concentration. Response to the agonist is then measured beginning with the addition of the lowest dose of agonist to the bath. Each dose is equilibrated in the bath for 2 to 6 minutes in order to assure a steady state response, prior to proceeding to the next higher dose.

Measurement of the effectiveness of smooth muscle relaxant compositions may then be determined by measurement of the smooth muscle relaxation response, in a manner analogous to contractile response. See generally Wang, Poon and Pang, *J. Pharm. Exp. Ther.* 265:112–119, 1993 (incorporated herein by reference in its entirety). Briefly, tissue is first contracted with an agonist such as phenylephrine, usually at a concentration which results in 90% of the tissue's maximum contractile response (referred to as $EC_{90}$). At the steady state phase of the contractile response to the agonist, a cumulative dose-response curve for the smooth muscle relaxant may be determined. For each concentration of relaxant, a steady state is achieved and the relaxation response measured. The effective concentration (EC) of a relaxant is the concentration that produces relaxation of a contraction previously induced by an agonist. For example, the $EC_{50}$ of a relaxant is the effective concentration of the relaxant required to relax a pre-contracted muscle to 50% of its maximum contractile response.

As described in more detail below, transition-metal nitrosyl complexes of the present invention have been demonstrated to be effective in the relaxation of smooth muscle in vitro. In particular, a series of transition-metal nitrosyl complexes were tested for their ability to relax pre-constricted rat aortic rings in vitro. All of the transition-metal nitrosyl complexes completely and dose-dependently relaxed phenylephrine pre-constricted aortae with efficacies similar to that of sodium nitroprusside. The results of the in vitro relaxation experiments are presented in Example 5 and Table 1. (See Example 5 for experimental detail.)

Likewise, in vivo tests may also be readily developed and utilized in order to determine the efficacy (and therapeutically effective amount) of the transition-metal nitrosyl complexes described above. For example, within one aspect of the present invention, a series of transition-metal nitrosyl complexes were tested in vivo for their ability to reduce the mean arterial blood pressure of conscious rats in vivo. Briefly, as described in greater detail below in Example 6, conscious, unrestrained rats were intravenous bolus injected with the transition-metal nitrosyl complexes. Five of the complexes were determined to dose-dependently reduce mean arterial pressure with maximum depressor effects which ranged from −36 to −59 mm Hg. Maximum depressor effects of sodium nitroprusside and nitroglycerin under similar conditions were −58 and −56 mm Hg, respectively. Three of the complexes exhibited potencies similar to, or greater than, that of nitroglycerin, and two of the complexes were found to be more potent than sodium nitroprusside. The results of the effects of the transition-metal nitrosyl complexes on the depression of mean arterial pressure in conscious rats in vivo are summarized in Example 5 and Table 1.

In addition to determining efficacy of transition-metal nitrosyl complexes in either in vitro or in vivo tests, it is also generally preferably to determine whether the composition induces tolerance. For example, within one embodiment of the invention, induction of tolerance by the transition-metal nitrosyl complex described above may be readily determined by exposing rat aortic rings to a transition-metal nitrosyl complex prior to relaxation determinations. More specifically, as described in greater detail 10 below in Example 7, intact rat aortic rings were pre-incubated with a typical transition- metal nitrosyl complex for one hour prior to examination of its concentration-relaxation effect in phenylephrine-preconstricted conditions. Unlike the relaxation response of nitroglycerin, the relaxation response of the transition-metal nitrosyl complexes was not diminished by pre-exposure of the aortic ring to the complex. The results indicate that tolerance develops less rapidly with the transition-metal nitrosyl complexes of the present invention than with nitroglycerin.

As noted above, transition-metal nitrosyl complexes of the present invention may be readily administered to a warm-blooded animal in order to relax a variety of smooth muscles. For example, within one aspect of the present invention, therapeutically effective amounts of a transition-metal nitrosyl complex may be administered to a warm-blooded animal in order to relax vascular smooth muscles. Through such methods, transition-metal nitrosyl complexes may be utilized in order to treat a variety of vascular disorders, including for example, hypertension, angina pectoris, and congestive heart failure.

The present invention also provides methods for relaxing nonvascular smooth muscle through the administration of the transition-metal nitrosyl complexes described above. For example, within one aspect of the present invention methods are provided for treating impotence, comprising the step of administering to a warm-blooded animal a transition-metal nitrosyl complex as described above. The effectiveness of the transition-metal nitrosyl complexes described above for the treatment of impotence may readily be evaluated through both in vitro and in vivo investigation. More specifically, in vitro evaluation may be accomplished utilizing corpus cavernosum excised from the penis of a rabbit, which is then dissected free from the tunica albuginea, cut into strips and mounted at resting tension. Phenylephrine-precontracted strips may be used in procedures similar to those described above, and in the examples, in order to construct dose-response curves for the transition-metal nitrosyl complexes.

Similarly, in vivo studies may likewise be utilized in order to test the efficacy of the transition-metal nitrosyl complexes described above in the treatment of impotence. Briefly, previous in vivo studies involving the systemic or central administration of low doses of apomorphine and other dopaminergic agonists, have shown that penile erection and yawning can be reliably induced in rats (Heaton et al., *J. Urol.* 145:1099–102, 1991). Therefore, in vivo studies may be utilized in order to investigate the utility of the transition-metal nitrosyl complexes of the present invention to facilitate apomorphine-induced penile erection in rats. For example, within one embodiment of the invention rats are individually placed in Plexiglas cages which have a mirror arranged in an oblique position to enhance observation. Pretreatment of the rats with a transition-metal nitrosyl complex may then be utilized to generate dose-response curves for apomorphine-induced rat penile erections.

Within another aspect of the present invention, methods are provided for enhancing learning and memory in warm-blooded animals, comprising the step of administering to a warm-blooded animal one of the above-described transition-metal nitrosyl complexes. The efficacy of such complexes in enhancing memory and learning may be readily ascertained through a variety of tests, including, for example, the Morris water maze performance test for rats. See Morris, *Learn Motiv.* 12:239–60, 1981; Decker and Majchrzak, *Psychopharmacol.* 107:530–34, 1992. Briefly, rats are given daily injections of various doses of transition-metal nitrosyl complexes at a time just prior to swimming sessions. The rats are then trained several times daily over a period of several days in a pool filled with warm milk. In each training trial, the rats are given a short period to find a submerged escape platform placed in one of the quadrants of the pool. Those not locating the platform will be guided to it. The mean escape latency on each training day may be determined as an index of information acquisition. The amount of time the rat spends in the training quadrant where the escape platform had been located during training will be indicative of acquired spatial information. The effect of transition-metal nitrosyl complexes on acquired spatial information may reflect the utility of these complexes in learning and memory.

Transition-metal nitrosyl complexes of the present invention have demonstrated beneficial vasodilation properties through their capacity to relax blood vessels in vitro and depress blood pressure in vivo. Furthermore, the complexes are as effective in vasodilation as existing nitrovasodilators, nitroglycerin and sodium nitroprusside. Additionally, the complexes do not appear to cause the adverse effect of tolerance associated with nitroglycerin nor toxicity associated with either nitroglycerin or sodium nitroprusside.

The following examples are offered by way of illustration, and not by way of limitation.

EXAMPLES

Examples 1–4 describe the preparation of the transition-metal nitrosyl complexes. All manipulations of compounds described in Examples 14 were performed under an atmosphere of prepurified dinitrogen or argon. All solvents were distilled from appropriate drying agents and degassed prior to use. Standard Schlenk and glove-box techniques were used throughout. Unless otherwise indicated, all other reactions and manipulations were carried out in a well ventilated fume hood. In these examples, the following abbreviations are used: THF, tetrahydrofuran; $CH_2Cl_2$, dichloromethane; IR, infrared spectrum; v refers to frequency; EIMS, electron impact mass spectroscopy; $P^+$ refers to parent ion; $^1H$ NMR, proton nuclear magnetic resonance; $CDCl_3$, deuteriochloroform; mp, melting point; FAB, fast atom bombardment; $P(OMe)_3$, trimethylphosphite; $C_5H_{11}N$, pip, piperidine; $C_5H_5N$, py, pyridine.

Examples 5–7 present in vitro and in vivo results of the evaluation of the efficiency of the transition-metal nitrosyl complexes in relaxing blood vessels and lowering blood pressure. Sprague-Dawley rats (300–400g) were used for all experiments. Each group consisted of 1–6 rats for the in vivo experiments and 3–6 aortic rings for the in vitro experiments. Each aortic ring was from a different rat.

EXAMPLE 1

The Synthesis of Transition-Metal Nitrosyl Complexes with Formula $L_3M(NO)_yX_2$ Example 1 presents the syntheses of the transition-metal nitrosyl complexes generally represented by the formula $L_3M(NO)_yX_{3-y}$ where y is 1: $L_3M(NO)X_2$.

A. Preparation of Dicarbonyl($\eta^5$-cyclopentadienyl)nitrosyl Complexes of Chromium, Molybdenum, and Tungsten Briefly, a 200-mL, three-necked flask is fitted with a nitrogen inlet and stirrer and is thoroughly flushed with prepurified dinitrogen. A dry THF solution (50 mL) containing 4.18 g of sodium cyclopentadienide, $Na[C_5H_5]$ is syringed into the flask, and $Cr(CO)_6$ (11.00 g, 50.0 mmol) and 100 mL of di-n-butyl ether are added. (In the case of molybdenum and tungsten the di-n-butyl ether is not added.) The flask is then equipped with a Leibig condenser and the reaction mixture is refluxed with vigorous stirring for 12 h. During this time, the reaction vessel is shaken occasionally to reintroduce any sublimed $Cr(CO)_6$ into the refluxing reaction mixture. The final reaction mixture is allowed to cool to room temperature and filtered, and the pale-yellow solid thus collected is washed with diethyl ether (3×10 mL), and dried under nitrogen. The excess $Cr(CO)_6$ and any di-n-butyl ether remaining in this solid are removed by sublimation at 90° C./0.005 torr onto a water-cooled probe. The $Na[(\eta^5-C_5H_5)M(CO)_3]$ complexes of molybdenum and tungsten are freed of any unreacted hexacarbonyl in a similar fashion, and all three sodium salts are used without further purification.

The preparations of all three $(\eta^5-C_5H_5)M(CO)_2(NO)$ complexes from their corresponding $[(\eta^5-C_5H_5)M(CO)_3]^-$ anions are similar. The experimental procedure using the tungsten complex dicarbonyl($\eta^5$-cyclopentadienyl)nitrosyltungsten, is given below.

A 300-mL, three-necked flask is equipped with a nitrogen inlet, an addition funnel, and a stirrer. It is charged with $Na[(\eta^5-C_5H_5)W(CO)_3]$ (17.3 g, 48.5 mmol) and THF (120 mL). A THF solution (50 mL) containing Diazald (N-methyl-N-nitroso-p-toluenesulfonamide, Aldrich Chemical Co.) (10.4 g, 48.6 mmol) is syringed into the addition funnel. The solution of Diazald is added dropwise over a period of 15 minutes and the solvent is removed in vacuo. Sublimation of the resulting brown residue at 50°–60° C./0.005 torr onto a water-cooled probe for three days affords $(\eta^5-C_5H_5)W(CO)_2(NO)$ (13.6 g, 84% yield).

The corresponding chromium and molybdenum complexes are obtained similarly in yields of 60 and 93% respectively. The compounds are orange to orange-red solids readily soluble in organic solvents. The solids are stable in air for short periods of time and indefinitely under dinitrogen.

Analysis calculated for $C_5H_5Cr(CO)_2(NO)$: C, 41.39; H, 2.48; N, 6.90. Found: C, 41.40; H, 2.60; N, 6.70. IR ($CH_2Cl_2$): $v_{CO}$ 2020, 1945; $v_{NO}$ 1680 cm$^{-1}$. EIMS (probe temperature 120° C.): m/z 203 [$P^+$].

Analysis calculated for $C_5H_5Mo(CO)_2(NO)$: C, 34.03; H, 2.04; N, 5.67. Found: C, 34.28; H, 2.24; N, 5.54. IR ($CH_2Cl_2$): $v_{CO}$ 2020, 1937; $v_{NO}$ 1663 cm$^{-1}$. EIMS (probe temperature 120° C.): m/z 249 [$P^+$].

Analysis calculated for $C_5H_5W(CO)_2(NO)$: C, 25.10; H, 1.50; N, 4.18. Found: C, 25.29; H, 1.70; N, 4.13. IR ($CH_2Cl_2$): $v_{CO}$ 2010, 1925; $v_{NO}$ 1655 cm$^{-1}$. EIMS (probe temperature 120° C.): m/z 319 [$P^+$].

B. Preparation of Dicarbonyl($\eta^5$-permethylcyclopentadienyl)nitrosyl Complexes of Molybdenum and Tungsten The permethylated complexes, $(\eta^5-C_5Me_5)M(CO)_2(NO)$ (M=Mo, W) are prepared in a manner similar to that of their cyclopentadienyl analogues except that $Li[C_5Me_5]$ is used instead of $Na[C_5H_5]$, and that higher temperatures (100° C.) are required to effect their sublimation.

Analysis calculated for $C_{10}H_{15}Mo(CO)_2(NO)$: C, 36.17; H, 4.55; N, 4.22. Found: C, 36.17; H, 4.60; N, 4.30. IR ($CH_2Cl_2$): $v_{NO}$ 1659 cm$^{-1}$. EIMS (probe temperature 120° C.): m/z 333 [$P^+$]. $^1H$ NMR ($CDCl_3$) d 1.95 (s).

Analysis calculated for $C_{10}H_{15}W(CO)_2(NO)$: C, 22.93; H, 1.92; N, 5.34. Found: C, 22.96; H, 1.87; N, 5.26. IR ($CH_2Cl_2$): $v_{NO}$ 1690 cm$^{-1}$. EIMS (probe temperature 120° C.): m/z 421 [$P^+$].

EXAMPLE 2

The Synthesis of Transition-Metal Nitrosyl Complexes with Formula $L_3M(NO)_2X$ This example presents the synthesis of the transition-metal nitrosyl complexes generally represented by the formula $L_3M(NO)_yX_{3-y}$ where y is 2: $L_3M(NO)_2X$.

A. Preparation of Chloro($\eta^5$-cyclopentadienyl)dinitrosyl Complexes of Chromium, Molybdenum, and Tungsten Approximately 2–3 mL of nitrosyl chloride is condensed into a 5-mL graduated cold trap held at −78° C. It is then allowed to melt so that its volume can be measured, and it is distilled under static vacuum into a 100-mL, two-necked flask held at −78° C. until just prior to use when it is allowed to warm to room temperature.

All three $(\eta^5-C_5H_5)M(NO)_2Cl$ complexes are prepared in a similar manner, but to achieve maximum yields of the chromium and molybdenum compounds, the reactions should be performed at −78° C. The molybdenum complex (chloro($\eta^5$-cyclopentadienyl)nitrosylmolybdenum), on the other hand, can be obtained in excellent yields even at room temperature as disclosed below.

A 200-mL, three-necked flask, equipped with a stirrer, a nitrogen inlet, and an addition funnel, is charged with $(\eta^5-C_5H_5)Mo(CO)_2(NO)$ (6.5 g, 26 mmol) and $CH_2Cl_2$ (100 mL). The nitrosyl chloride solution (typically containing 2.3 mL (50 mmol) of nitrosyl chloride in 30 mL of $CH_2Cl_2$) is added dropwise to the stirred reaction mixture. Gas evolution occurs and the orange solution becomes dark green. The reaction is monitored by infrared spectroscopy and the nitrosyl chloride solution is added until the carbonyl absorptions of the initial organometallic reactant have disappeared. It is extremely important that a stoichiometric amount of nitrosyl chloride (ClNO) be used, since even a slight excess of ClNO reduces significantly the yields of the desired products, especially in the cases of the chromium and tungsten complexes. Conversely, if an insufficient quantity of ClNO is added, the separation of any unreacted ($\eta^5$-$C_5H_5$)M(CO)$_2$(NO) from the desired chloronitrosyl complex is difficult. The final reaction mixture is concentrated in vacuo to approximately 30 mL, and is filtered through a short (3×5 cm) Florisil column. The column is washed with $CH_2Cl_2$ until the washings are colorless, and the combined filtrates are then concentrated in vacuo to a volume of 30 mL. Dry hexanes are added until crystallization appears to be complete; approximately 100–125 mL of hexanes are required. The resulting green crystals are collected by filtration, washed with hexane (2×15 mL) and dried under dinitrogen to obtain analytically pure ($\eta^5$-$C_5H_5$)Mo(NO)$_2$Cl (6.0 g, 89% yield). The chromium and tungsten compounds are obtained similarly (except that the reaction flask is maintained at −78° C. during the addition of the ClNO) in yields of 77 and 72%, respectively.

Analysis calculated for $C_5H_5Cr(NO)_2Cl$: C, 28.26; H, 2.37; N, 13.18; Cl, 16.68. Found: C, 28.2; H, 2.55; N, 12.86; Cl, 16.99. IR ($CH_2Cl_2$): $v_{NO}$ 1816, 1711 cm$^{-1}$. EIMS (probe temperature 120° C.): m/z 212 [P$^+$]. mp 144° C. (dec).

Analysis calculated for $C_5H_5Mo(NO)_2Cl$: C, 23.42; H, 1.96; N, 10.92. Found: C, 23.53; H, 1.90; N, 10.70. IR ($CH_2Cl_2$): $v_{NO}$ 1759, 1665 cm$^{-1}$. EIMS (probe temperature 120° C.): m/z 258 [P$^+$]. mp 116° C.

Analysis calculated for $C_5H_5W(NO)_2Cl$: C, 17.44; H, 1.46; N, 8.13; Cl, 10.29.. Found: C, 17.68; H, 1.68; N, 8.10; Cl, 10.26. IR ($CH_2Cl_2$): $v_{NO}$ 1733, 1650 cm$^{-1}$. EIMS (probe temperature 120° C.): m/z 343 [P$^{+1. mp}$ 127° C. (dec).

B. Preparation of Nitrito($\eta^5$-cyclopentadienyl) dinitrosylchromium

CpCr(NO)$_2$Cl (1.0 g, 4.7 mmol) (Cp=$\eta^5$-$C_5H_5$) is dissolved in 50 mL distilled water. A distilled water solution (25 mL) of AgNO$_2$ (0.72 g, 4.7 mmol) is added to the stirred, green solution of CpCr(NO)$_2$Cl. A flocculent white solid forms immediately. Stirring is continued for 30 min, and then the mixture is filtered to remove the white solid. The filtered solution is extracted with 3×50 mL of $CH_2Cl_2$. The extracts are combined, dried with anhydrous $Na_2SO_4$, and filtered. The solvent is removed in vacuo until the solution reaches a volume of 20 mL. Twenty mL of hexanes are then added, and the mixture is cooled to −30° C. to induce crystallization. This procedure results in the formation of analytically pure CpCr(NO)$_2$(ONO) (0.51 g, 49% yield).

Analysis calculated for $C_5H_5Cr(NO)_2(ONO)$: C, 26.92; H, 2.26; N, 18.83. Found: C, 27.21; H, 2.15; N, 18.76. IR ($CH_2Cl_2$): $v_{NO}$ 1825, 1719 cm$^{-1}$. $^1$H NMR (CDCl$_3$) d 5.78 (s). EIMS (probe temperature 120° C.): m/z 223 [P$^+$].

EXAMPLE 3

The Synthesis of Transition-Metal Nitrosyl Complexes with Formula L$_3$M(NO)XL

This example presents the syntheses of the transition-metal nitrosyl complexes generally represented by the formula L$_3$M(NO)$_y$X$_{3-y}$ where y is 1 and X$_2$ is XL: L$_3$M(NO)XL.

A. Preparation of Iodo($\eta^5$-cyclopentadienyl) nitrosylchromium Dimer

To a stirred orange solution of CpCr(CO)$_2$(NO) (2.03 g, 10.0 mmol) is added solid I$_2$ (1.24 g, 4.90 mmol). Reaction occurs after 5 min as evidenced by gas evolution and a color change of the reaction mixture to green-brown. After being stirred for 1 h to ensure completion of the reaction, the mixture is taken to dryness under reduced pressure. Crystallization of the residue from $CH_2Cl_2$/hexanes affords dark green [CpCr(NO)I]$_2$ (2.35 g, 88% yield)

Analysis calculated for $[C_5H_5Cr(NO)I]_2$: C, 21.92; H, 1.84; N, 5.11; I, 46.33. Found: C, 22.00; H, 1.77; N, 5.00; I, 46.08. IR ($CH_2Cl_2$): $v_{NO}$ 1673 cm$^{-1}$. EIMS (probe temperature 120 ° C.): m/z 548 [P$^+$]. mp 119° C. (dec).

B. Preparation of Iodo($\eta^5$-cyclopentadienyl)nitrosyl(L) chromium (L=P(OMe)$_3$, pip, py)

Olive green [CpCr(NO)I]$_2$ (0.27 g, 0.50 mmol) is dissolved in $CH_2Cl_2$ (20 mL). To the stirred solution, 0.081 mL (1.0 mmol) of pyridine is added by syringe. The color changes from dark green to a brighter green over the period of 30 min. The solution is reduced in volume to approximately 10 mL, and then filtered through alumina (1.5×3 cm) supported on a medium-porosity frit. The column is washed with $CH_2Cl_2$ until the washings are colorless. Hexanes (30 mL) are added, and the solution is reduced in volume until crystallization is initiated. The mixture is then cooled to −30° C. overnight to complete crystallization. The solvent is removed by cannulation, and the dark green crystals are washed with pentane (3×15 mL). This solid is dried in vacuo to obtain 0.32 g (90% yield) of CpCr(NO)(py)I.

Analysis calculated for $C_{10}H_{10}N_2OCrI$: C, 34.02; H, 2.85; N, 7.93. Found: C, 34.15; H, 2.82; N, 7.80. IR (Nujol mull): $v_{NO}$ 1651 cm$^{-1}$. FAB mass spectrum: m/z 353 [P$^+$].

The preparation of CpCr(NO)(L)I where L=piperidine and L=P(OMe)$_3$ is analogous to above where L=pyridine.

Data for CpCr(NO)[P(OMe)$_3$]I: 0.35 g, 88% yield. Analysis calculated for $C_8H_{14}NO_4PCrI$: C, 24.13; H, 3.54; N, 3.52. Found: C, 24.19; H, 3.54; N, 3.49. IR (Nujol mull): $v_{NO}$ 1650 cm$^{-1}$. FAB mass spectrum: m/z 398 [P$^+$].

Data for CpCr(NO)(pip)I. Analysis calculated for $C_{10}H_{16}N_2OCrI$: C, 33.44; H, 4.49; N, 7.80. Found: C, 33.23; H, 4.46; N, 7.70. IR (Nujol mull): $v_{NO}$ 1651 cm$^{-1}$. FAB mass spectrum: m/z 359 [P$^+$]

EXAMPLE 4

The Synthesis of Transition-Metal Nitrosyl Complexes with Formula[M(NO)$_y$X$_2$]$_n$ This example presents the syntheses of transition-metal nitrosyl complexes generally represented by the formula [M(NO)$_2$X$_y$]$_2$ when M is a Group 6 transition metal, y is 2, and when M is a Group 8 transition metal, y is 1.

A. Preparation of Dichloro Dinitrosyl Complexes of Molybdenum and Tungsten

A 500-mL, three-necked round-bottom flask is equipped with a gas inlet and an addition funnel, and is charged with powdered W(CO)$_6$ (17.6 g, 50.0 mmol). The entire system is then thoroughly purged with prepurified dinitrogen and $CH_2Cl_2$ (90 mL) is added. The addition funnel is charged with a $CH_2Cl_2$ solution of ClNO (6 mL, 120 mmol). 6 mL of the ClNO solution is added to the flask, and a small amount of air (0.50 mL) is added by syringe to initiate the reaction. The addition of the ClNO solution is carried out in a dropwise manner, the reaction being monitored by IR spectroscopy. When the IR band at 1977 cm$^{-1}$ due to the W(CO)$_6$ starting material has disappeared, the addition is halted, and the solution is allowed to stir for a further 30 min. The green precipitate which has formed is collected on a glass frit, washed with CH$_2$Cl$_2$ and dried in vacuo to obtain [W(NO)$_2$Cl)$_2$]$_n$ (14.52 g, 92% yield) as an olive green powder.

Analysis calculated for WN$_2$O$_2$Cl$_2$: C, 0.00; H, 0.00; N, 8.90; Cl, 22.52. Found: C, 0.23; H, 0.00; N, 8.88; Cl, 21.97. IR (Nujol mull): $v_{NO}$ 1794, 1680 cm$^{-1}$.

The preparation of [Mo(NO)$_2$Cl$_2$]$_n$ is analogous to [W(NO)$_2$Cl]$_2$]$_n$ above. Analysis calculated for MoN$_2$O$_2$Cl$_2$: N, 12.4; Cl, 31.3; Mo, 42.3. Found: N, 12.7; Cl, 32.2; Mo, 41.1. IR (Nujol mull): $v_{NO}$ 1805, 1690 cm$^{-1}$. 91% yield based on MO(CO)$_6$.

B. Preparation of Iodo(dinitrosyl)iron Dimer

Dry acetone (250 mL) and 33.5 g (0.3 mol) of iron powder are added to a 1000-mL three-necked round-bottom flask equipped with a gas inlet, a 500-mL pressure-equalizing addition funnel equipped with a bubbler, and a mechanical stirrer. A solution containing 38.1 g (0.1 mol) of I$_2$ in Et$_2$O (300 mL) is then added through the addition funnel dropwise over a period of 45–74 min. After the addition is complete, NO gas is introduced into the flask at a rate sufficient to maintain a flow of gas of about one bubble per second through the bubbler. Stirring must be sufficiently vigorous to ensure efficient uptake of the NO gas. The end of the reaction is marked by the cessation of the absorption of nitric oxide as determined by the use of the bubbler.

The solvent is removed in vacuo. When the black residue is completely dry, the desired product is sublimed onto a water-cooled probe. The flask should be heated slowly (2° C./min) to 90° C. Explosive decomposition can take place if the heating rate is excessive. The product can be scraped off the probe in an inert atmosphere drybox and stored under dinitrogen.

Analysis calculated for [Fe(NO)$_2$I]$_2$: Fe, 23.0; I, 52.3. Found: Fe, 23.4; I 51.8. IR (Nujol mull): $v_{NO}$ 1807, 1766 cm$^{-1}$.

EXAMPLE 5

Relaxation of Blood Vessels Utilizing Transition-Metal Nitrosyl Complexes

Example 5 presents the results of the evaluation of the efficacy of the transition metal nitrosyl complexes in blood vessel relaxation. In these in vitro experiments, phenylephrine pre-constricted rat aortae were subjected to increasing doses of the transition-metal nitrosyl complexes, and the relaxation of the rat aortae measured. Concentration-response (relaxation) curves were prepared, and the ability of the transition-metal nitrosyl complexes to relax the blood vessels were compared and related to nitroglycerin and sodium nitroprusside. The results of these experiments are reported in terms of EC$_{50}$ (effective concentration to produce a 50% relaxation response) and E$_{max}$ (percent relaxation of phenylephrine-induced contraction) and are tabulated in Table 1.

Briefly, rats were sacrificed by a blow on the head followed by exsanguination. The thoracic aorta was removed and cleared of connective tissues. Four ring segments of 0.5 cm length each were prepared from one aorta and suspended in separate organ baths. Each ring was connected to a Grass FT-03-C force-displacement transducer (Quincy, Mass.) for isometric recording with a pre-load of 1 g and was equilibrated for 1 hr (with 3 washouts) in normal Krebs solution (pH 7.4) at 37° C. with a gas mixture of 95% O$_2$ and 5% CO$_2$. The Krebs solution had the following composition (10$^{-3}$M): NaCl, 118; glucose, 11; KCl, 4.7; CaCl$_2$, 2.5; NaHCO$_3$, 25; KH$_2$PO$_4$, 1.2; MgCl$_2$6H$_2$O, 1.2.

Phenylephrine (10$^{-6}$M, EC$_{90}$) was added to the baths and at 15–20 min later, at the steady state phase of the contractile response to phenylephrine, a cumulative concentration-response curve of sodium nitroprusside or a metal nitrosyl complex was constructed using sequential doubling of the drug concentration. Each concentration of a drug was left in the bath for 2-4 min to ensure a plateau response is reached. The time taken to complete each concentration-response curve was approximately 20 min. FIG. 1A shows concentration-response curves of CpCr(NO)$_2$Cl and CpMo(NO)$_2$Cl.

TABLE 1

The effects of metal nitrosyl complexes on relaxation of pre-constricted aortic rings in vitro and depression of mean arterial pressure in conscious rats in vivo

| | | In vitro | | | In vivo | | |
|---|---|---|---|---|---|---|---|
| Entry | Name | n | EC$_{50}$ ($\mu$M) | E$_{max}$ (%) | n | ED$_{50}$ ($\mu$g/kg) | E$_{max}$ (mmHg) | Toxic dose (mg/kg) |
| 1 | Na nitroprusside | 6 | 0.052 | −128 | 6 | 8.4 | −58 | 10,000[a] |
| 2 | Nitroglycerin | 6 | 0.30 | −104 | 6 | 200 | −56 | — |
| 3 | CpCr(NO)$_2$Cl | 6 | 0.11 | −118 | 6 | 4.4 | −42 | 2,000[a] |
| 4 | CpMo(NO)$_2$Cl | 6 | 17 | −113 | 6 | 400 | −59 | 25,600[b] |
| 5 | CpW(NO)$_2$Cl | 6 | 2.0 | −122 | 2 | 2976 | −36 | 40,000[c] |
| 6 | CpCr(NO)(pip)I | 5 | 0.45 | −110 | — | — | — | — |
| 7 | CpW(NO)(CO)$_2$ | 3 | 2.5 | −107 | 3 | — | biphasic[d] | 500[a] |
| 8 | [Mo(NO)$_2$Cl$_2$]$_n$ | 6 | 81 | −119 | 2 | >5120 | no effect | — |
| 9 | [W(NO)$_2$Cl$_2$]$_n$ | 6 | 335 | −108 | 1 | >5120 | no effect | — |
| 10 | [Fe(NO)$_2$I]2 | 6 | 20 | −108 | 2 | 554 | −51 | 5120[c] |
| 11 | CpCr(NO)$_2$(ONO) | 6 | 0.1 | −98 | 2 | 1.5 | −45 | 1280[a] |

[a]denotes dose which caused convulsion
[b]denotes dose which caused death
[c]denotes dose which caused neither convulsion nor death.
[d]denotes depressor followed by pressor response.

EXAMPLE 6

Depression of Arterial Blood Pressure Utilizing Transition-Metal Nitrosyl Complexes Example 6 describes the results of the determination of the efficacy of the transition-metal nitrosyl complexes in reducing blood pressure of conscious, unrestrained rats. In these in vivo experiments, the depression of rat arterial pressure was measured as a function of transition-metal nitrosyl complex dose. Dose-response (pressure depression) curves were constructed and the capacities of the transition-metal nitrosyl complexes to reduce arterial pressure were compared and related to nitroglycerin and sodium nitroprusside. The results of these experiments are reported in terms of $ED_{50}$ (effective dose to produce a 50% pressure depression response) and $E_{max}$ (maximum decrease in blood pressure) and are summarized in Example 5, Table 1.

The rats were anaesthetized with halothane (4% in air for induction and 1.5% in air for surgery). A polyethylene cannula (PE50) was inserted into the left iliac artery for the measurement of mean arterial pressure (MAP) by a pressure transducer (P23DB, Gould Statham, Calif.). A PE50 cannula was also inserted into the iliac vein for the administration of the vehicle or a drug. The rats were then put into a small cage and given >6 hr to recover from the effects of anaesthesia and surgery before use. The rats were allowed to move freely during the recovery phase as well as during the conduction of the experiments as described in Wang and Pang, *Br. J. Pharmacol.* 103:2004–8, 1991. Only one dose-response curve of a metal nitrosyl complex, sodium nitroprusside, nitroglycerin or vehicle (0.9% NaCl solution or dimethylsulfoxide solution) was constructed in each rat. All drugs or vehicle were intravenous bolus injected at dose-intervals of 3–7 min, to allow the recovery of depressor responses, before the injection of the next higher dose.

Figure 1B:
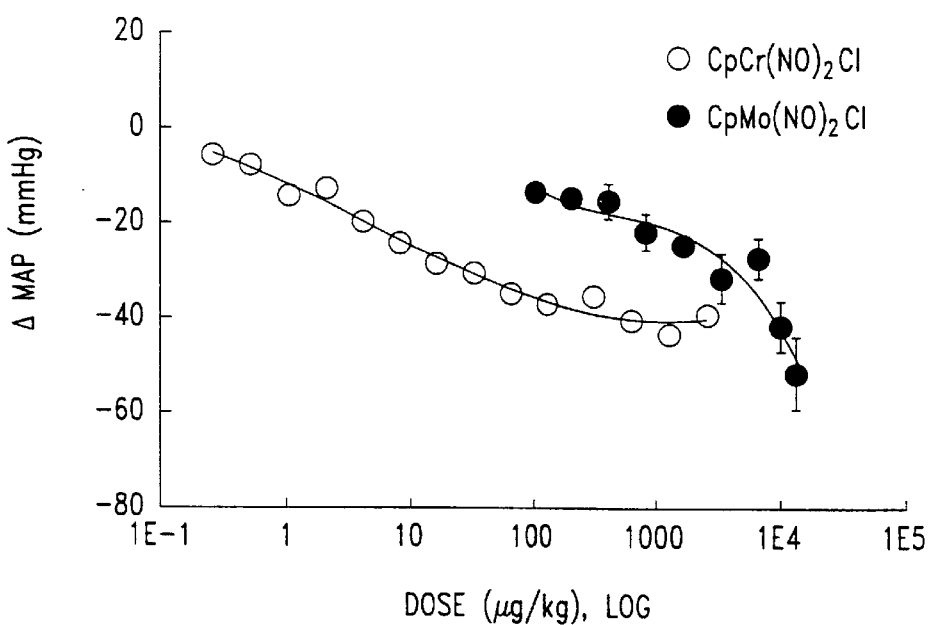

Five of the eight metal nitrosyl complexes tested were found to lower blood pressure in a dose-related manner. The maximum depressor responses of some of the metal nitrosyl complexes were similar to those of nitroglycerin and sodium nitroprusside. The potencies (inverse of $ED_{50}$) of some of the metal nitrosyl complexes were similar to or greater than those of nitroglycerin and sodium nitroprusside. FIG. 1B shows concentration-response curves of $CpCr(NO)_2Cl$ and $CpMo(NO)_2Cl$.

EXAMPLE 7

Example 7 presents the results of pre-exposing the rat aortae to the transition-metal nitrosyl complexes to evaluate the development of tolerance. In these experiments, the rat aortic rings were pretreated with a transition-metal nitrosyl complex prior to the measurement of dose-dependent relaxation as described above in Example 5.

In this study, the vehicles, $CpCr(NO)_2Cl$ ($10^{-6}M$), or nitroglycerin ($3\times10^{-4}M$) was added to the baths for 1 h, followed by the washout of drug or vehicle, preconstriction with phenylephrine and the construction of a concentration-relaxation curve of $CpCr(NO)_2Cl$.

Figure 2A:
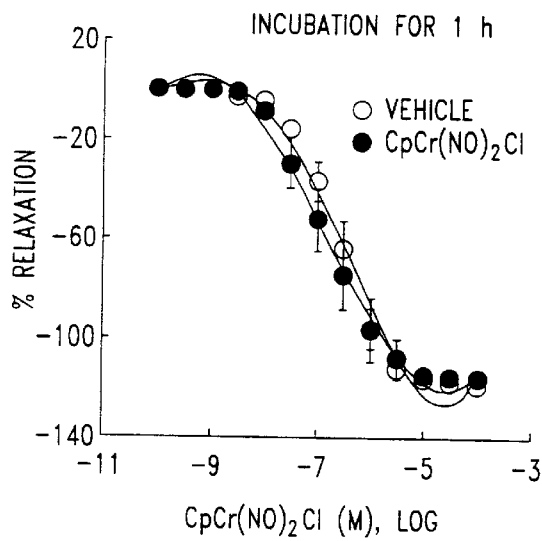
FIG. 2 is a graph which illustrates the effects of preincubation with vehicle, CpCr$(NO)_2$Cl, and nitroglycerin on subsequent relaxation responses to CpCr$(NO)_2$Cl, nitroglycerin, and sodium nitroprusside of phenylephrine-preconstricted rat aortic rings.
Figure 2C:
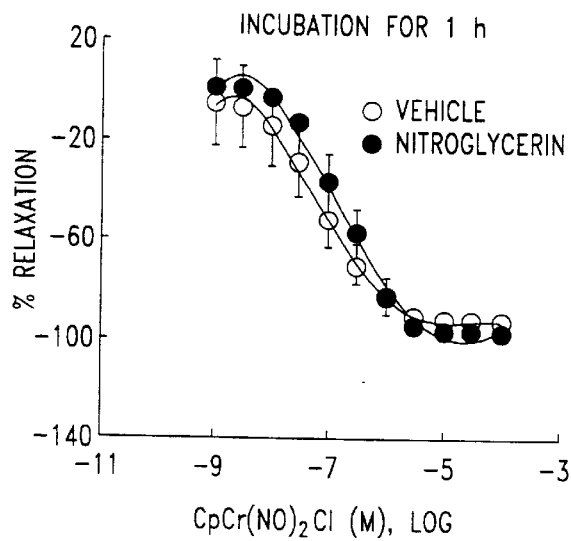
Figure 2B:
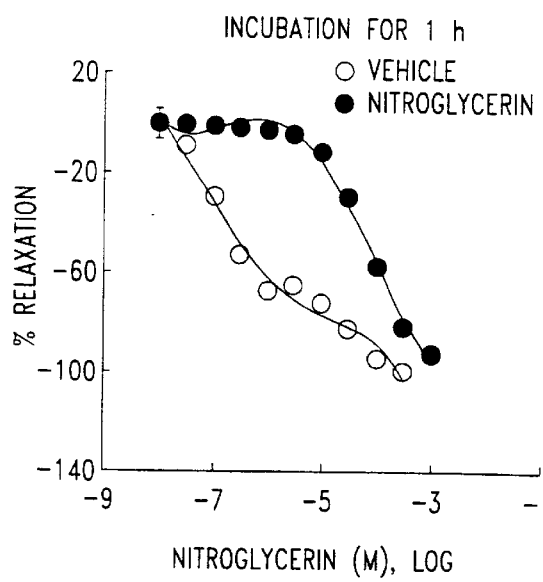
Figure 2D:
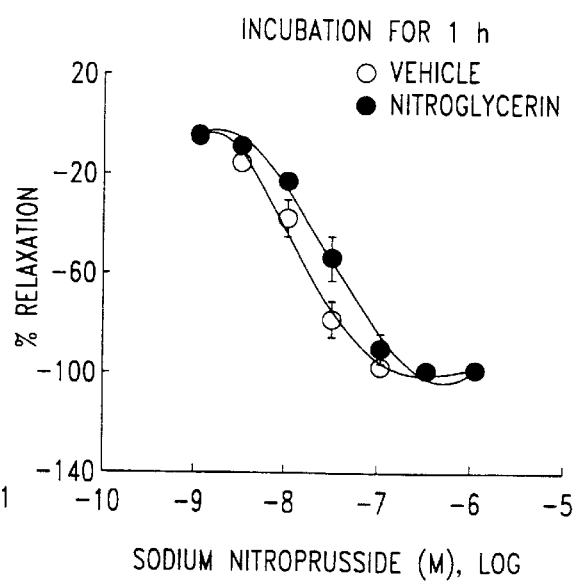

The results show that the pre-incubation with $CpCr(NO)_2Cl$ did not alter the $EC_{50}$ or $E_{max}$ of the compound (see FIG. 2A), suggesting that tolerance to the tested drug does not readily develop. Pre-incubation with nitroglycerin shifted the nitroglycerin dose-response curve to the right with $EC_{50}$ significantly increased and $E_{max}$ unaltered. See FIG. 2B. This shows that tolerance develops to nitroglycerin. Pre-exposure to nitroglycerin did not alter the $EC_{50}$ or $E_{max}$ of $CpCr(NO)_2Cl$, showing that no cross-tolerance exists between nitroglycerin and $CpCr(NO)_2Cl$. See FIG. 2C. Pre-exposure to nitroglycerin slightly, but statistically significantly ($p<0.05$), increased the $EC_{50}$ of sodium nitroprusside, suggesting a small degree of cross-tolerance between these two drugs. See FIG. 2D.

From the foregoing, it will be appreciated that, although specific embodiments of the invention have been described herein for purposes of illustration, various modifications may be made without deviating from the spirit and scope of the invention. Accordingly, the invention is not limited except by the appended claims.

We claim:

1. A method for relaxing smooth muscle in a warm-blooded animal, comprising administering to said animal a therapeutically effective amount of a transition-metal nitrosyl complex represented by the formula

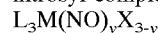

$L_3M(NO)_yX_{3-y}$ wherein L is a two-electron Lewis base or $L_3$ is a six-electron Lewis base, M is a Group 6 or 8 transition-metal, wherein y is 1 or 2, X is either a halide or pseudohalide, and when y is 1, $X_2$ is either $L_2$ or XL.

2. A method for treating hypertension in a warm-blooded animal, comprising administering to said animal a therapeutically effective amount of a transition-metal nitrosyl complex represented by the formula

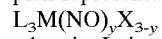

$L_3M(NO)_yX_{3-y}$ wherein L is a two-electron Lewis base or $L_3$ is a six-electron Lewis base, M is a Group 6 or 8 transition-metal, wherein v is I or 2. [and when y is 2, X is either a halide or pseudohalide, and when y is 1, $X_2$ is either $L_2$ or XL.

3. A method for treating angina pectoris in a warm-blooded animal, comprising administering to said animal a therapeutically effective amount of a transition-metal nitrosyl complex represented by the formula

$L_3M(NO)_yX_{3-y}$ wherein L is a two-electron Lewis base or $L_3$ is a six-electron Lewis base, M is a Group 6 or 8 transition-metal, wherein v is 1 or 2, X is either a halide or pseudohalide, and when y is 1, $X_2$ is either $L_2$ or XL.

4. A method for treating congestive heart failure in a warm-blooded animal, comprising administering to said animal a therapeutically effective amount of a transition-metal nitrosyl complex represented by the formula

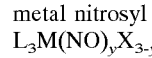

$L_3M(NO)_yX_{3-y}$ wherein L is a two-electron Lewis base or $L_3$ is a six-electron Lewis base, M is a Group 6 or 8 transition-metal, wherein v is 1 or 2, X is either a halide or pseudohalide, and when y is 1, $X_2$ is either $L_2$ or XL.

5. A method for treating impotence in a warm-blooded animal, comprising administering to said animal a therapeutically effective amount of a transition-metal nitrosyl complex represented by the formula

$L_3M(NO)_yX_{3-y}$ wherein L is a two-electron Lewis base or $L_3$ is a six-electron Lewis base, M is a Group 6 or 8 transition-metal, wherein y is 1 or 2 [and when y is 2, X is either a halide or pseudohalide, and when y is 1, $X_2$ is either $L_2$ or XL.

6. A method for relaxing smooth muscle in a warm-blooded animal, comprising administering to said animal a therapeutically effective amount of a transition-metal nitrosyl complex represented by the formula

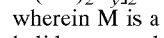

$[M(NO)_2X_y]_2$ wherein M is a Group 6 or 8 transition-metal, X is either a halide or pseudohalide, and when M is a Group 6 transition-metal, y is 2, and when M is a Group 8 transition-metal, y is 1.

7. A method for treating hypertension in a warm-blooded animal, comprising administering to said animal a therapeutically effective amount of a transition-metal nitrosyl complex represented by the formula
$[M(NO)_2X_y]_2$
wherein M is a Group 6 or 8 transition-metal, X is either a halide or pseudohalide, and when M is a Group 6 transition-metal, y is 2, and when M is a Group 8 transition-metal, y is 1.

8. A method for treating angina pectoris in a warm-blooded animal, comprising administering to said animal a therapeutically effective amount of a transition-metal nitrosyl complex represented by the formula
$[M(NO)_2X_y]_2$
wherein M is a Group 6 or 8 transition-metal, X is either a halide or pseudohalide, and when M is a Group 6 transition-metal, y is 2, and when M is a Group 8 transition-metal, y is 1.

9. A method for treating congestive heart failure in a warm-blooded animal, comprising administering to said animal a therapeutically effective amount of a transition-metal nitrosyl complex represented by the formula
$[M(NO)_2X_y]_2$
wherein M is a Group 6 or 8 transition-metal, X is either a halide or pseudohalide, and when M is a Group 6 transition-metal, y is 2, and when M is a Group 8 transition-metal, y is 1.

10. A method for treating impotence in a warm-blooded animal, comprising administering to said animal a therapeutically effective amount of a transition-metal nitrosyl complex represented by the formula
$M(NO)_2X_y]_2$
wherein M is a Group 6 or 8 transition-metal, X is either a halide or pseudohalide, and when M is a Group 6 transition-metal, y is 2, and when M is a Group 8 transition-metal, y is 1.

11. A pharmaceutical composition, comprising a transition-metal nitrosyl complex represented by the formula
$[M(NO)_2X_y]_2$
wherein M is a Group 6 or 8 transition-metal, X is either a halide or pseudohalide, and when M is a Group 6 transition-metal, y is 2, and when M is a Group 8 transition-metal, y is 1, and a pharmaceutically acceptable carrier or diluent.

12. The pharmaceutical composition of claim 11 wherein X is a halide selected from the group consisting of fluoride, chloride, bromide and iodide.

13. The pharmaceutical composition of claim 11 wherein X is a pseudohalide selected from the group consisting of nitrite, nitrate, and cyanide anion.

14. The pharmaceutical composition of claim 11 wherein the transition-metal nitrosyl complex is iodo(dinitrosyl)iron dimer.

* * * * *